United States Patent
Pelzer et al.

(10) Patent No.: US 8,007,081 B2
(45) Date of Patent: Aug. 30, 2011

(54) DEVICE AND METHOD FOR DELIVERING A FLUID IN FORM OF A HIGH-SPEED MICRO-JET

(75) Inventors: Heiko Pelzer, Erkelenz (NL); Klaus Reimann, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/305,392

(22) PCT Filed: Jun. 19, 2007

(86) PCT No.: PCT/IB2007/052341
§ 371 (c)(1),
(2), (4) Date: Dec. 18, 2008

(87) PCT Pub. No.: WO2008/001268
PCT Pub. Date: Jan. 3, 2008

(65) Prior Publication Data
US 2009/0201344 A1    Aug. 13, 2009

(30) Foreign Application Priority Data
Jun. 28, 2006   (EP) .................................... 06116178

(51) Int. Cl.
*B41J 2/045* (2006.01)
*B41J 2/14* (2006.01)
*B41J 2/16* (2006.01)

(52) U.S. Cl. ......................................... 347/68; 347/48

(58) Field of Classification Search .................... 347/70, 347/11, 48
See application file for complete search history.

(56) References Cited

U.S. PATENT DOCUMENTS

| | | | |
|---|---|---|---|
| 4,184,169 A | 1/1980 | Bansal | |
| 5,812,163 A | 9/1998 | Wong | |
| 5,828,394 A * | 10/1998 | Khuri-Yakub et al. | 347/72 |
| 6,290,339 B1 * | 9/2001 | Furlani et al. | 347/68 |
| 6,291,927 B1 | 9/2001 | Percin | |
| 6,513,917 B1 * | 2/2003 | Matsuda et al. | 347/70 |
| 6,833,112 B2 | 12/2004 | Hoummady | |
| 2004/0260234 A1 | 12/2004 | Srinivasan | |
| 2005/0018019 A1 | 1/2005 | Miyazawa | |
| 2005/0069429 A1 | 3/2005 | Sugahara | |
| 2005/0140742 A1* | 6/2005 | Nakamura | 347/68 |
| 2005/0179342 A1 | 8/2005 | Higuchi | |
| 2006/0012645 A1 | 1/2006 | Nagashima | |

FOREIGN PATENT DOCUMENTS

| | | |
|---|---|---|
| EP | 1243418 A1 | 9/2002 |
| JP | 01283154 A1 | 11/1989 |
| WO | 9853777 A1 | 12/1998 |

\* cited by examiner

*Primary Examiner* — Matthew Luu
*Assistant Examiner* — Lisa M Solomon

(57) ABSTRACT

A device and method for delivering a fluid in the form of a high-speed micro-jet includes a container for accommodating a fluid which is to be delivered through an orifice of the container, and an actuator cooperating with the container. The actuator includes a thin-film transducer membrane, where the transducer membrane is divided into at least two transducer elements. The transducer elements form a transducer array in which each transducer element corresponds to a certain portion of the transducer membrane.

11 Claims, 4 Drawing Sheets

DEVICE AND METHOD FOR DELIVERING A FLUID IN FORM OF A HIGH-SPEED MICRO-JET

Figure 1:
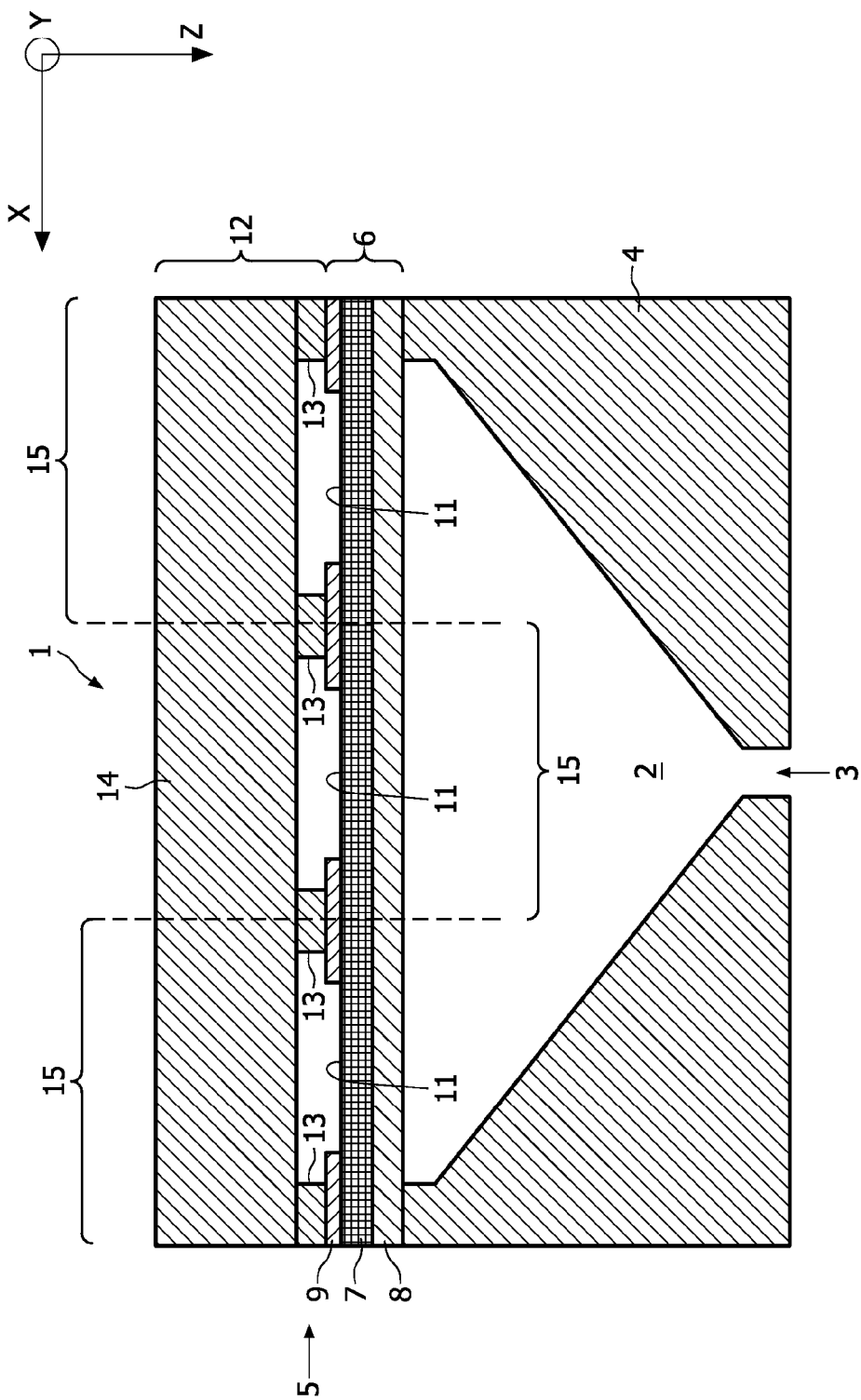

The present invention relates to a device and method for delivering a fluid in the form of a high-speed micro-jet.

Traditionally, the dominant method of delivering medication into the human body has been by oral ingestion of pills. Other methods include injections and pulmonary and transmucosal drug delivery. Another method of drug delivery is transdermal drug delivery. Transdermal drug delivery is the delivery of the medical substance directly across the skin barrier. Transdermal delivery has many advantages over other drug delivery methods, such as the avoidance of first pass metabolism, etc.

The main barrier to diffusion of pharmaceuticals across the skin is the outermost layer of the skin, the stratum corneum. Various methods of enhancing transdermal drug delivery across the stratum corneum have been devised, among them the use of enhancing agents or stimulants such as chemical, voltage charge, ultrasonic waves, thermal treatments, microneedles, and laser assist techniques. However, these techniques do not offer the capability of time-dependent dosage delivery.

Another mechanism of drug delivery is the use of needleless injections or high-speed jet injectors. Jet injectors move the solution to be injected at high speed and eject the solution as a jet, penetrating the stratum corneum and depositing the solution into the dermis and subcutaneous regions of the skin. While traditional high-speed jets are capable of transporting drugs across the stratum corneum, a drawback of this mechanism is that they deliver a large quantity of the drug which is delivered in a once-only jet injection.

There are new approaches for repetitively delivering small quantities of drugs by means of the high-speed jet mechanism. However, the devices in use are rather bulky and costly, since they use piezoelectric bulk transducers, e.g. made from Lead Zirconate Titanate (PZT) with the dimensions of 2×2×2 mm or 5×5×5 mm. Such piezoelectric bulk transducer contain a large amount of lead.

It is an object of the present invention to provide a small and low-cost device for delivering a fluid in the form of a high-speed micro-jet.

This object is achieved according to the invention by a device for delivering a fluid in the form of a high-speed micro-jet, comprising a container for accommodating a fluid which is to be delivered through an orifice of said container and further comprising an actuator cooperating with said container, characterized in that said actuator comprises a thin-film transducer membrane, wherein the transducer membrane is divided into at least two transducer elements, said transducer elements forming a transducer array in which each transducer element corresponds to a certain portion of the transducer membrane.

A core idea of the invention is the use of low-cost semiconductor thin-film technology to build low-cost devices for the delivery of fluids in the form of high-speed micro-jets. For this purpose, the thin-film transducer membrane is divided into at least two transducer elements in order to apply the pressure for generating high-speed micro-jets. Said transducer elements form a transducer array in which each transducer element corresponds to a certain portion of the transducer membrane. The transducer array may be one- or two-dimensional, i.e. the transducer elements may be arranged in a line to form a one-dimensional array, or in two dimensions to form a two-dimensional array.

Thin-film piezoelectric actuators can be provided in the form of low-cost thin film devices which can be manufactured by existing semiconductor technology. Such thin-film piezoelectric actuators comprise only very small amounts of lead. Such a reduction of the lead content is especially desired for environmental reasons.

The object of the present invention is also achieved by a method of delivering a fluid by means of a fluid-delivering device, the method comprising the step of applying a drive voltage to flex a transducer element of a thin-film transducer membrane of said device, said transducer membrane being divided into at least two transducer elements, said transducer elements forming a transducer array in which each transducer element corresponds to a certain portion of the transducer membrane, said transducer membrane being part of an actuator, said actuator cooperating with a fluid container such that the fluid is delivered through an orifice of the container when the transducer element is flexed.

These and other aspects of the invention will be further elaborated on the basis of the following embodiments which are defined in the dependent claims.

In preferred embodiments of the invention, the transducer element can be actuated by piezoelectric or electrostatic actuation. In the case of piezoelectric actuation the transducer membrane comprises a piezoelectric layer, and the transducer element is flexed by piezoelectric actuation of the piezoelectric layer through the application of an electric field to the piezoelectric layer. Both piezoelectric and electrostatic actuation are well known concepts in the field of thin-film transducer elements and render it possible to use low-cost semiconductor processes to manufacture transducer arrays as described in the present invention. A combination of piezoelectric and electrostatic actuation may be used.

In a preferred embodiment of the invention, each transducer element is provided with a dedicated support structure for obtaining an optimum translation of the piezoelectric layer. The support structures are used for separating the transducer membrane into single transducer elements that form the array structure. The array structure is used to define the stiffness and the total energy content of the transducer membrane. The stiffness is determined by the layer thickness of the transducer membrane, the Young's modulus of the materials constituting the transducer membrane, and the length of the membrane of the single transducer element in the main direction of longitudinal expansion/contraction of the piezoelectric layer. The total energy content is essentially determined by the piezo material itself, the applied voltage, the design of the electrodes, and the total volume of the piezoelectric layer. Thus, the larger the area of the piezoelectric layer or the more transducer elements, the more energy will be available. The stiffness of the single transducer element limits the pressure that can be applied to the fluid and determines the velocity of the micro-jets. The total available energy limits the amount of fluid that can be delivered in one stroke of the membrane. Consequently, small transducer elements are needed to obtain high-velocity micro-jets capable of, for example, perforating the stratum corneum, and a reasonable amount of transducer elements are needed to eject a reasonable amount of fluid in one stroke.

Another object of the present invention is to enhance the delivery speed of the fluid. This object of the present invention is achieved by the device as described above, which comprises a control unit adapted to apply the drive voltage separately to each transducer element. This object of the invention is also achieved by a method comprising the step of applying the drive voltage such that a defined pressure wave is generated in the container of said device and said pressure wave is focused on the orifice of said container. In other words, the array structure of the membrane transducer has the additional advantage that it renders possible an active focusing of the pressure wave in the drug on the at least one orifice of the fluid container. This increases the velocity of the microjet at a given drive voltage.

The present invention can be used in a medical environment, e.g. for transdermal drug delivery, e.g. for the delivery of peptides, proteins, and DNA-based therapeutic substances, and for pain management. Furthermore, the invention can be used for transdermal injection of liquids for cosmetic purposes. Furthermore, the invention can be used for ink jet printing devices.

Figure 2:
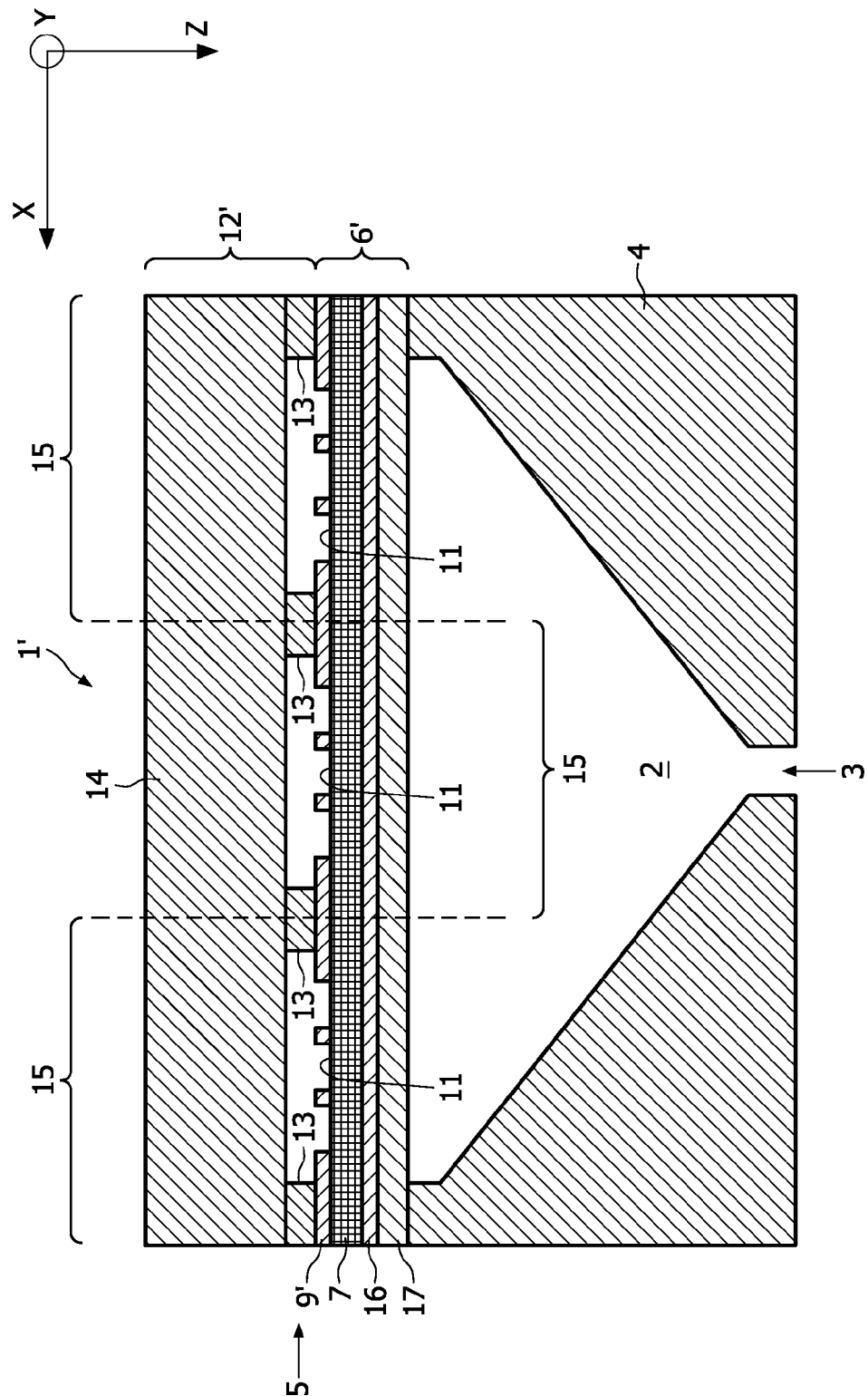
Figure 3:
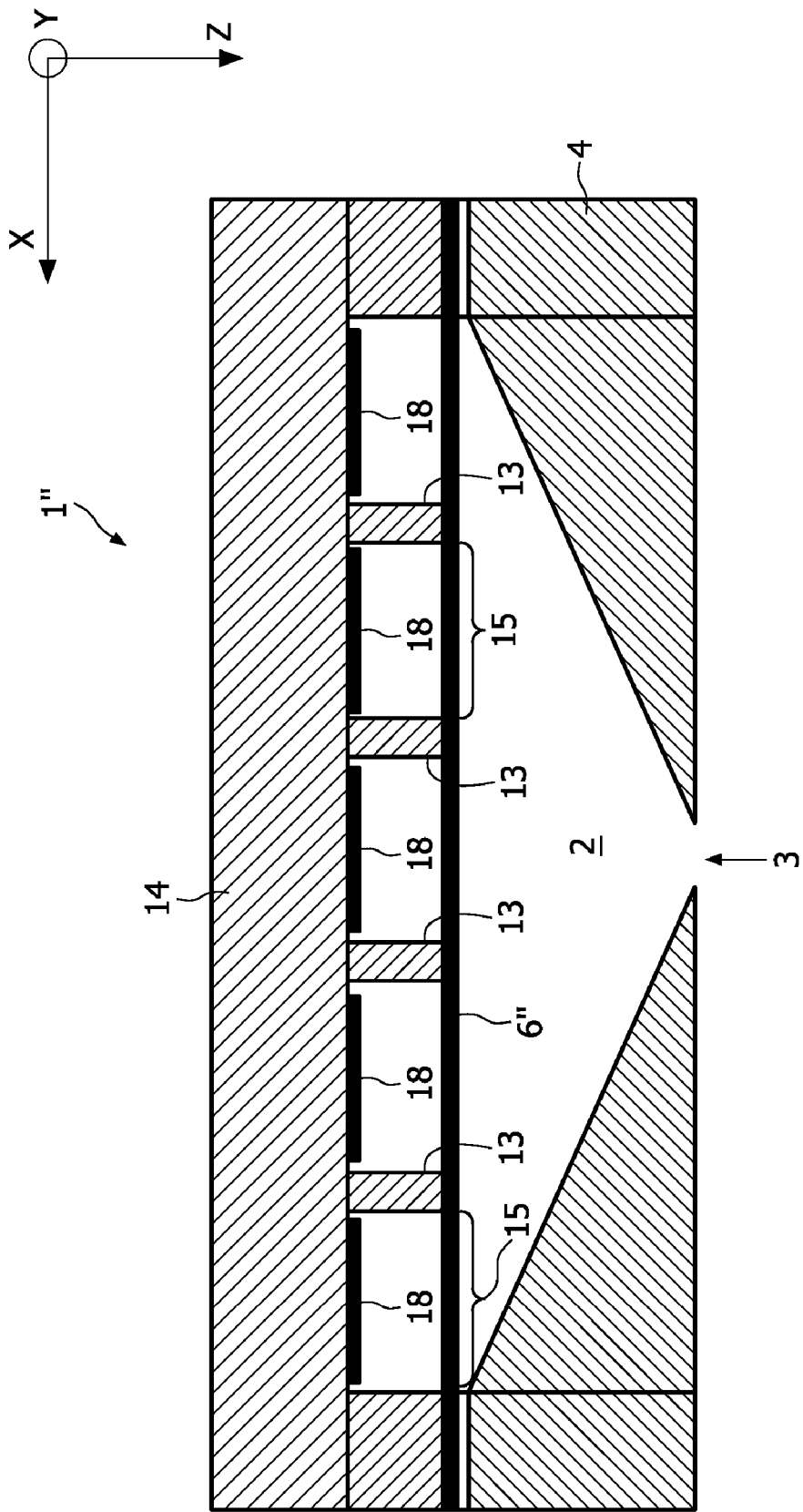
Figure 4:
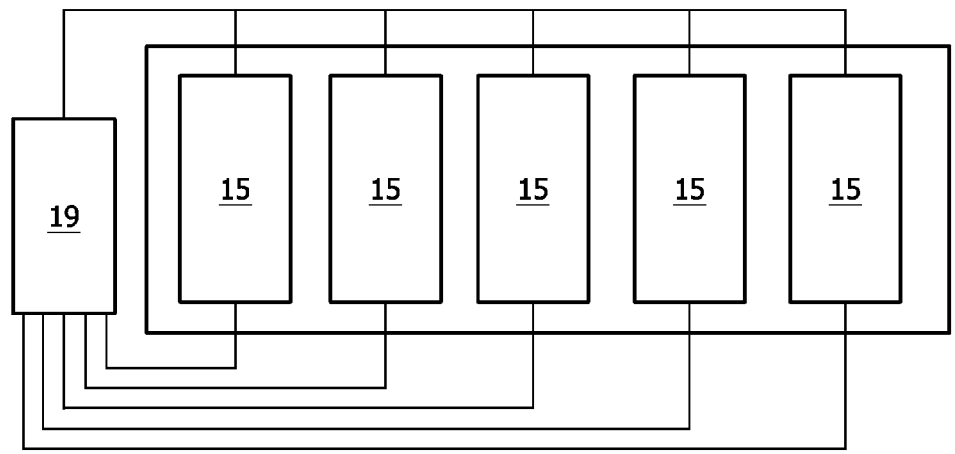
Figure 5:
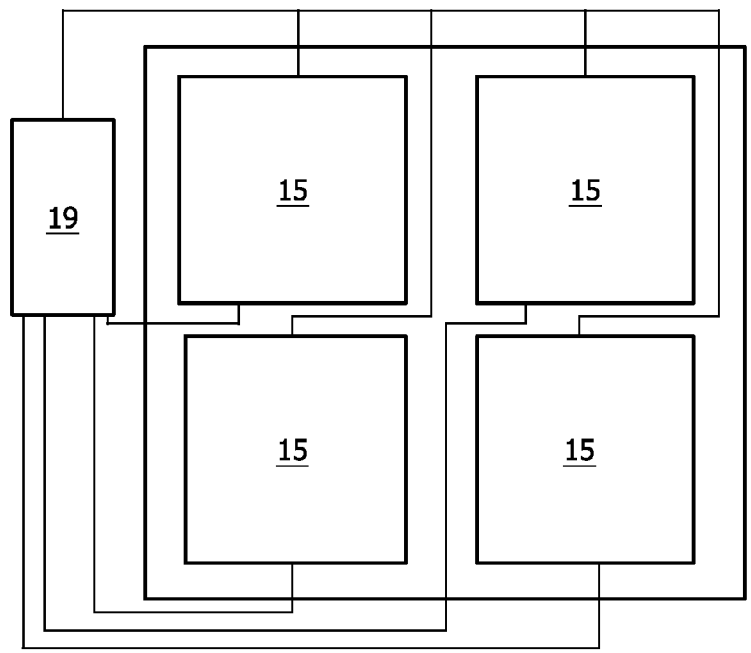

These and other aspects of the invention will be described in detail hereinafter, by way of example, with reference to the following embodiments and the accompanying drawings; in which:

FIG. 1 is a schematic illustration of a first embodiment of the fluid delivery device, FIG. 2 is a schematic illustration of a second embodiment of the fluid delivery device, FIG. 3 is a schematic illustration of a third embodiment of the fluid delivery device, FIG. 4 is a schematic illustration of a linear array of transducer elements, and FIG. 5 is a schematic illustration of a two-dimensional array of transducer elements.

A first fluid delivery device 1 is shown in FIG. 1. A fluid in the form of a liquid drug is used in the present embodiment. The delivery device 1 comprises a funnel-shaped container 2 for accommodating the drug, which is to be delivered through a nozzle 3. The container 2 is part of a base element 4. The nozzle 3 is positioned at the narrow end of the funnel. Other container shapes may be used as well. The device 1 further comprises an actuator 5 for cooperating with said container 2, which actuator 5 comprises a thin-film transducer membrane 6. The transducer membrane 6 closes off one side of the container 2, the nozzle 3 being located on the opposite side of the container 2. The transducer membrane 6 comprises a piezoelectric layer 7, a bottom electrode 8, and a top electrode 9. Both electrodes 8, 9 are provided in the form of conducting electrode layers (thin-film layers). The piezoelectric layer 7 is made of PZT with a thickness between 0.5 µm and 10 µm. Some other piezoelectric material may be used instead of PZT.

The bottom electrode 8 is unstructured and covers the complete lower surface of the PZT layer 7 towards the container 2. The top electrode 9 is structured such that it covers only portions of the upper surface of the PZT layer 7. In other words, there are areas 11 of the PZT layer's 7 upper surface which are not covered by the top electrode 9. Areas of the PZT layer's 7 upper surface which are covered by the top electrode 9 are provided with a support structure 12 comprising legs 13 or bars, said legs 13 or bars being connected to a rigid backplate 14. Thus, the PZT layer 7 is clamped between the bottom electrode 8 and the structured top electrode 9 by means of the support structure 12.

Depending on the structure of the top electrode 9 and the position of the support structure 12 relative to the transducer membrane 6, the transducer membrane 6 is partitioned into a number of transducer elements 15, each having a comparatively small effective surface area. Said transducer elements 15 form a transducer array in which each transducer element 15 corresponds to a certain portion of the transducer membrane 6. FIG. 1 shows three such transducer elements 15. The dimension of each transducer element 15 is defined by the position of the support structure 12 relative to the transducer membrane 6. The length of a transducer element 15 in an x-direction is given by the distance between two adjacent legs 13 or bars of the support structure 12. The distance between these legs 13 or bars in the x-direction essentially influences the stiffness of the transducer membrane 6, whereas the dimensioning in the y-direction can be rather different. In other words, the transducer membrane 6 is stiffened in that it is fixed in a defined way, i.e. along defined lines, to a support structure 12. The extension of a transducer element 15 in the x-direction of the membrane plane is between 10 µm and 1 mm.

The structuring of the top electrode 9 and the clamping of the transducer membrane 6 by means of the support structure 12 is done in a way so as to get the maximum translation of the longitudinal (x-direction) expansion/contraction of the PZT layer 7 into a vertical movement (z-direction) of the transducer membrane 6 in order to exert pressure on the liquid drug. In other words, the support structure 12 guarantees the required stiffness of each single transducer element 15. Furthermore, the existence of a sufficiently large number of cooperating small transducer elements 15 in the form of an array guarantees the delivery of a sufficiently large quantity of fluid.

Other electrode combinations are also possible, for example, both electrodes 8, 9 may be structured, or an unstructured top electrode 9 may be used, depending on the remaining composition of the transducer membrane 6.

The transducer membrane 6 with the transducer elements 15 and the support structure 12 is fixed on the container 2 for the liquid drug. Another possibility is that the entire container 2 or parts thereof belong to a semiconductor wafer structure, on which the electrodes 8, 9 and the piezoelectric layer 7 are provided by means of semiconductor thin film technology. This includes etching of the container 2 and structuring of the top electrode 9. In addition, the support structure 12, e.g. a structured silicon wafer with metallization, is glued or soldered on the structured top electrode 9 in order to stiffen the transducer membrane 6.

FIG. 1 shows a cross-section of a delivery device 1 with a one-dimensional transducer array in the x-direction. In order to deliver the liquid drug, a drive voltage is applied across the PZT layer 7. In other words, a drive voltage is applied to the electrodes 8, 9 in order to expand/contract the PZT layer 7 in the membrane plane, mainly using the expansion/contraction of the PZT layer 7 perpendicular to the electric field between top electrode 9 and bottom electrode 8. Using the support structure 12 upon which the transducer membrane 6 is fixed and the structured top electrode 9, the expansion/contraction of the PZT layer 7 is translated into the plane of the transducer membrane 6. The transducer elements 15 deflect perpendicularly to the plane of the transducer membrane 6, and a pressure is exerted on the liquid drug in the container 2 in the z-direction, forcing the drug from the container 2 through the nozzle 3. In another embodiment (not shown), further transducer elements 15 are positioned in the y-direction such that the transducer elements 15 form a two-dimensional array.

A control unit (not shown) is provided for applying the drive voltage, said control unit being connected to the actuator 5, in particular to the electrodes 8, 9 of the thin-film transducer membrane 6. A special technique may be applied for controlling the transducer elements 15 in one- or two-dimensional arrays. According to this technique, the transducer elements 15, of which each single one is selectively deformable, can be activated separately, i.e. controlled by means of a drive voltage, in order to achieve an active focusing of the pressure wave in the container 2. In other words, each transducer element 15 can be controlled separately by the control unit. The control unit is connected to each transducer element 15 for this purpose, which can be achieved by technology known from printed circuit boards. The control unit controls the transducer elements 15 such that a defined pressure wave is generated in the container 2 and said pressure wave is focused on the nozzle 3 of the container 2. In other words, the fluid pressure reaches its maximum at the nozzle 3. This is preferably achieved by first applying the drive voltage to the transducer elements 15 which are furthest from the nozzle 3 and continuing with applying the adjacent transducer elements 15, etc., such that a "phase shift" towards the nozzle 3 is achieved. The exact application of the drive voltage depends inter alia on the shape of the transducer array, the shape of the container 2, and the position of the nozzle 3 relative to the transducer membrane 6.

The internal control of the control unit is preferably achieved by means of a computer software comprising computer instructions adapted to control the drive voltage as described when the software is executed in a processing unit of the control unit. Alternatively, the method of controlling the drive voltages may be implemented in hardware, e. g. using one or more integrated circuits. The processing unit itself may comprise functional modules or units implemented in the form of hardware, software, or a combination of both.

In a further embodiment (not shown), the container 2 comprises more than one nozzle 3. In addition, there may be means for opening or closing the nozzles 3 in a defined way, which operation of the nozzles is preferably carried out so as to correspond to the dynamically controlled application of the drive voltage to the transducer elements 15.

In another embodiment of the invention, the entire delivery device 1 as illustrated in FIG. 1 is integrated into a housing (not shown) with a fluid reservoir, which reservoir is connected to the drug container 2 of the device 1 in order to refill it after ejection of fluid. In addition, this housing may contain a microprocessor-based control unit for controlling the activation of the device 1 and an energy source, e.g. a battery, as a power supply. The control unit can take over the function of applying the drive voltage as described above.

FIG. 2 shows another embodiment of the invention, in which the transducer membrane 6' comprises two membrane layers 16, 17 (e.g. made of $SiO_2$, $Si_3N_4$ or similar materials available in semiconductor production lines) forming the upper surface of the transducer membrane 6', the piezoelectric (e.g. PZT) layer 7, and a single electrode layer forming a top electrode 9'. Alternatively, only one membrane layer may be used and/or the piezoelectric layer 7 may be structured (not shown). The structuring of the top electrode 9' and the clamping by means of the support structure 12' are again performed so as to get the maximum translation of the longitudinal (x-direction) expansion/contraction of the piezoelectric layer 7 into vertical movement (z-direction) of the transducer membrane 6 in order to exert pressure on the drug.

In the embodiment shown in FIG. 1, the electric field is aligned between top and bottom electrode 9, 8 and runs in the z-direction, i.e. vertical to the direction of longitudinal expansion/contraction (x-direction) of the piezoelectric layer 7. In this case the $d_{31}$ piezo coefficient is used for the expansion/contraction. In contrast thereto, in the embodiment of FIG. 2, the electric field is aligned with the direction of expansion/contraction (x-direction), i.e. the electric field runs in the x-direction. Consequently the $d_{33}$ piezo coefficient is used in this case. A comparatively high drive voltage is applied to the top electrode 9', preferably using an increased membrane temperature, leading to a comparatively large deflection of the transducer membrane 6'.

A number of membrane layers 16, 17 as shown in FIG. 2 may also be used in the embodiment illustrated in FIG. 1.

Such additional membrane layers 16, 17 can help to increase the stiffness and the deflection of the transducer membrane 6.

FIG. 3 shows another embodiment of the invention. The operation of the illustrated fluid delivery device 1" is based on electrostatic actuation. A voltage can be applied to one or more of five electrodes 18 and the single membrane 6". The electrodes 18 are located on the backplate 14 and between the legs 13, which serve as supports for the single membrane 6", which runs across the container 2. The membrane 6" may comprise a single conductive layer or a stack of several layers, wherein only one layer has to be electrically conductive. By controlling the voltage between the electrodes 18 and the membrane 6" in an independent way, it is possible to flex portions of the membrane 6" located opposite to the associated electrodes 18 independently of each other. Such portions serve as transducer elements 15 according to the present invention.

The transducer elements 15 can be arranged so as to form one- or two-dimensional arrays. A one-dimensional, i.e. linear array is illustrated in FIG. 4 and a two-dimensional array is illustrated in FIG. 5. With the linear array a defined pressure wave can be generated along a straight line in the container 2. With the two-dimensional array a defined pressure wave can be generated along a straight line as well. Additionally, however, the actuation can be focused on a certain spot. The transducer elements 15, a controller 19 for controlling the transducer elements 15, and the connecting lines between the controller 19 and the transducer elements 15 are shown for each embodiment.

Recapitulating, the present invention suggests a fluid delivery device 1 which uses low-cost standard thin-film technology to provide a thin piezoelectric layer 7. In order to achieve a sufficient deflection of such a thin piezoelectric layer 7, the membrane 6 is stiffened by means of dedicated support structures 12 which subdivide the membrane 6 into an array of smaller membrane elements 15 which exhibit the stiffness needed. Additionally, said membrane elements 15 can be controlled independently so as to generate a pressure wave for an accelerated fluid output.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. It will furthermore be evident that the word "comprising" does not exclude other elements or steps, that the words "a" or "an" do not exclude a plurality, and that a single element, such as a computer system or another unit, may fulfil the functions of several means recited in the claims. Any reference signs in the claims shall not be construed as limiting the claim concerned.

REFERENCE NUMERALS 1 fluid delivery device
2 container
3 nozzle
4 base element
5 actuator
6 transducer membrane
7 piezoelectric layer
8 bottom electrode 9 top electrode
10 (free)
11 uncovered area
12 support structure
13 leg
14 backplate
15 transducer element
16 membrane layer
17 membrane layer
18 electrode
19 controller

The invention claimed is:

1. A device for delivering a fluid in the form of a high-speed micro-jet, comprising:
    a container for accommodating the fluid which is to be delivered through an orifice of said container; and
    an actuator cooperating with said container;
    wherein said actuator comprises a thin-film transducer membrane, and wherein the transducer membrane is divided into at least two transducer elements, said transducer elements forming a transducer array in which each transducer element corresponds to a certain portion of the transducer membrane for delivering the fluid through the orifice,
    wherein the at least two transducer elements are configured to by activated to provide a maximum fluid pressure at the orifice by activation of edge transducer elements furthest from the orifice and continuing activation of adjacent transducer elements adjacent to the edge transducer elements.

2. The device as claimed in claim 1, wherein each transducer element is provided with a dedicated support structure.

3. The device as claimed in claim 1, wherein said transducer membrane comprises a piezoelectric layer and the transducer element is flexed by piezoelectric actuation.

4. The device as claimed in claim 1, wherein the transducer element is flexed by electrostatic actuation.

5. The device as claimed in claim 1, further comprising a control unit adapted to apply the drive voltage separately to the each transducer element.

6. A method of delivering a fluid by a fluid-delivering device, comprising the acts of:
    applying a drive voltage to flex a transducer element of a thin-film transducer membrane of said device, said transducer membrane being divided into at least two transducer elements, said transducer elements forming a transducer array in which each transducer element corresponds to a certain portion of the transducer membrane, said transducer membrane being part of an actuator; and
    delivering the fluid through an orifice of a container by said actuator cooperating with the fluid container, wherein the act of applying the drive voltage activates the two transducer elements to provide a maximum fluid pressure at the orifice by activation of edge transducer elements furthest from the orifice and continuing activation of adjacent transducer elements adjacent to the edge transducer elements.

7. The method as claimed in claim 6, wherein the act of applying the drive voltage generates a defined pressure wave in the container of said device, and wherein said pressure wave is focused on the orifice of said container.

8. The device of claim 3, wherein the piezoelectric layer deflects perpendicularly to a plane of the transducer membrane in response to an electric field applied perpendicularly to the plane.

9. The device of claim 3, wherein the piezoelectric layer deflects parallel to a plane of the transducer membrane in response to an electric field applied parallel to the plane.

10. The method of claim 6, wherein the act of applying the drive voltage generated an electric field which is perpendicular to a plane of the transducer membrane.

11. The method of claim 6, wherein the act of applying the drive voltage generated an electric field which is parallel to a plane of the transducer membrane.

* * * * *